United States Patent
Scheer et al.

(10) Patent No.: US 7,445,699 B2
(45) Date of Patent: Nov. 4, 2008

(54) GAS SENSOR

(75) Inventors: Heiner Scheer, Berghuelen (DE);
Carsten Springhorn, Stuttgart (DE);
Hans-Joerg Renz,
Leinfelden-Echterdingen (DE); Frank Haag, Hussenhofen (DE); Walter Strassner, Schorndorf (DE); Lothar Diehl, Gerlingen (DE); Thomas Moser, Schwieberdingen (DE); Stefan Rodewald, Ditzingen (DE); Marten Mamey, Oehringen (DE); Jürgen Karle, Rutesheim (DE)

(73) Assignee: Robert Bosch GmbH, Stuttgart (DE)

( * ) Notice: Subject to any disclaimer, the term of this patent is extended or adjusted under 35 U.S.C. 154(b) by 856 days.

(21) Appl. No.: 10/493,199

(22) PCT Filed: Oct. 4, 2002

(86) PCT No.: PCT/DE02/03770

§ 371 (c)(1),
(2), (4) Date: Sep. 28, 2004

(87) PCT Pub. No.: WO03/036281

PCT Pub. Date: May 1, 2003

(65) Prior Publication Data

US 2005/0034986 A1 Feb. 17, 2005

(30) Foreign Application Priority Data

Oct. 17, 2001 (DE) ................ 101 51 328

(51) Int. Cl.
*G01N 27/41* (2006.01)
*G01N 27/409* (2006.01)
(52) U.S. Cl. .............. 204/425; 204/426; 73/23.32

(58) Field of Classification Search ............... 204/424,
204/425, 426, 427; 205/783.5; 73/23.31,
73/23.32
See application file for complete search history.

(56) References Cited

U.S. PATENT DOCUMENTS

| | | | | |
|---|---|---|---|---|
| 5,298,147 A | * | 3/1994 | Nakae et al. | 204/424 |
| 5,314,604 A | * | 5/1994 | Friese et al. | 204/410 |
| 5,505,837 A | | 4/1996 | Friese et al. | |
| 5,885,429 A | * | 3/1999 | Friese et al. | 204/427 |
| 5,902,469 A | * | 5/1999 | Kato et al. | 204/425 |
| 6,068,748 A | | 5/2000 | Berger et al. | |
| 6,334,946 B1 | * | 1/2002 | Mabuchi et al. | 205/784 |
| 6,767,442 B1 | * | 7/2004 | Scheer et al. | 204/425 |
| 2003/0136676 A1 | * | 7/2003 | Miwa et al. | 204/426 |

FOREIGN PATENT DOCUMENTS

| | | |
|---|---|---|
| DE | 38 41 611 | 6/1990 |
| DE | 43 11 851 | 10/1994 |

(Continued)

*Primary Examiner*—Kaj K Olsen
(74) *Attorney, Agent, or Firm*—Kenyon & Kenyon LLP

(57) ABSTRACT

A gas sensor for detecting at least one physical magnitude of a gas, in particular of exhaust gases of an internal combustion engine, is proposed, which includes a sensor element having an electrochemical cell. The electrochemical cell includes a first solid electrolyte member on which a first electrode and a second electrode are applied. The first and the second electrode are electrically connected by means of the first solid electrolyte member. The first electrode is in contact with the gas. The area of the first electrode is smaller than the area of the second electrode.

15 Claims, 3 Drawing Sheets

FOREIGN PATENT DOCUMENTS

| | | |
|---|---|---|
| DE | 44 08 504 | 9/1995 |
| DE | 44 39 901 | 5/1996 |
| DE | 199 41 051 | 3/2001 |
| DE | 199 60 329 | 7/2001 |
| WO | WO 01/16588 A1 * | 3/2001 |

* cited by examiner

GAS SENSOR

This application is a 371 National Stage Entry of PCT/DE02/03770 filed on Oct. 4, 2002.

FIELD OF THE INVENTION

The present invention is based on a gas sensor.

BACKGROUND INFORMATION

A gas sensor is known from the German Published Patent Application No. 199 41 051, for example, for use in analyzing the exhaust gas of internal combustion engines. The gas sensor regulates the air/fuel ratio of combustion mixtures in motor vehicle engines and is provided with a sensor element that combines a concentration cell (Nernst cell) with an electrochemical pump cell.

The concentration cell of the sensor element has a measuring electrode arranged in a measuring-gas region and a reference electrode located in a reference-gas region. The two electrodes are applied on a solid electrolyte member and electrically connected via the solid electrolyte member. The measuring-gas region in which the measuring electrode is located is connected to the exhaust gas outside of the sensor element via a diffusion barrier and a gas-access hole. The reference-gas region is in contact with a reference atmosphere via an opening situated on the side of the sensor element facing away from the measuring-gas region. Measuring-gas region and reference-gas region are arranged in the same plane of stratification of the sensor element configured as layer system and are separated by a gas-tight separation member. At different oxygen partial pressures in the measuring-gas region and the reference-gas region, a so-called Nernst voltage is generated between the measuring electrode and the reference electrode. When the oxygen partial pressure in the reference-gas chamber is constant, the oxygen partial pressure in the measuring-gas region may be determined from the Nernst voltage.

The pump cell of the sensor element includes an annular outer pump electrode arranged on an outer surface of the sensor element and exposed to the exhaust gas and an also annular inner pump electrode located in the measuring-gas region on the solid electrolyte member. The inner pump electrode may coincide with the measuring electrode of the Nernst cell or may be electrically connected to it. The outer pump electrode has a greater outer radius and a smaller inner radius than the inner pump electrode, so that the surface of the outer pump electrode is larger than the surface of the inner pump electrode. By means of supply lines, the electrodes are electrically connected to contact surfaces arranged on the side of the sensor element facing away from the electrodes. An insulation layer electrically insulates the supply lines of the electrodes, in particular the supply line of the outer pump electrode, from the solid electrolyte member.

When a pump voltage is applied between the outer pump electrode and the inner pump electrode, the pump cell pumps oxygen ions via the solid electrolyte member out of the measuring-gas region into the exhaust gas or vice versa from the exhaust gas into the measuring-gas region. The pump voltage is regulated by an external circuit elements in such a way that a Nernst voltage of approximately 450 mV is available between the electrodes of the Nernst cell, which corresponds to an oxygen partial pressure in the measuring-gas region of lambda=1 (stoichiometric air-fuel ratio). Accordingly, oxygen is pumped out of the measuring-gas region if lean exhaust gas is present (lambda>1), the pump current flowing in the pump cell being limited by the diffusion stream of the oxygen molecules flowing through the diffusion barrier into the measuring-gas region. In the case of rich exhaust gas (lambda<1), oxygen is pumped into the measuring-gas region, and the pump current flowing in the pump cell is limited by the diffusion stream of the gas molecules that flow through the diffusion barrier and consume oxygen in the measuring-gas region (the oxygen pumped into the measuring-gas region reacts there with the oxygen-consuming gas molecules). In lean exhaust gas, the diffusion stream is proportional to the oxygen concentration of the exhaust gas, and in the case of rich exhaust gas it is proportional to the concentration of oxygen-consuming gas molecules. Thus, it is possible to ascertain from the pump current the oxygen partial pressure of the exhaust gas, or the partial pressure of the gas molecules consuming oxygen.

From German Published Patent Application No. 199 60 329, a gas sensor having a similar sensor element is known. In contrast to the sensor element described in German Published Patent Application No. 199 41 051, the measuring-gas region and the reference-gas region are arranged in different planes of stratification. The surfaces of the outer pump electrode and the inner pump electrode are identical.

It is disadvantageous in such sensor elements that an overswinger or a counterswing is generated in the sensor signal in response to a change in the direction of the pump current, which occurs during operation of the gas sensor in a change from lean to rich exhaust gas, for example. This so-called $\lambda=1$ ripple has a detrimental effect on the evaluation of the sensor signal.

SUMMARY OF THE INVENTION

The gas sensor according to the independent claim has the advantage that the $\lambda=1$ ripple is considerably reduced or avoided entirely.

The sensor element includes an electrochemical cell, which has a first electrode (outer pump electrode) arranged on an outer surface, facing the gas, of the sensor element, and a second electrode (inner pump electrode, measuring electrode) arranged in a measuring-gas region, as well as a solid electrolyte member, which is situated between the two electrodes and electrically connects them to one another. The first electrode is directly exposed to the exhaust gas whose oxygen partial pressure is subject to strong fluctuations. In lean, that is to say, oxygen-rich exhaust gas, the solid electrolyte in the region of the first electrode has a high oxygen concentration as well. Since the oxygen in the solid electrolyte is present in the form of ions, a large charge quantity is formed in the region of the first electrode in the case of lean exhaust gas. Correspondingly, a small charge quantity is present in the region of the first electrode when the exhaust gas is rich and low in oxygen. In contrast, the second electrode is exposed to a largely constant oxygen partial pressure since an oxygen partial pressure of $\lambda=1$ is set in the measuring-gas region.

It has been shown that the charge quantity generated in the region of the first electrode in lean exhaust gas causes the $\lambda=1$ ripple when the pump voltage is reversed. Therefore, to lower the charge quantity, the area of the first electrode is reduced. Since the charge quantity at the second electrode is subject to fewer fluctuations, the area of the second electrode may be larger than the area of the first electrode without this increasing the $\lambda=1$ ripple.

In an advantageous manner, the first and second electrode are designed such that, apart from a reduction of the $\lambda=1$ ripple, a sufficiently low resistance between the first and second electrode is achieved as well. When the resistance is low, a relatively low pump voltage is enough to generate a pump voltage that is sufficient for the control to λ=1. Since a larger electrode surface means lower resistance, the second electrode therefore has considerably larger dimensions than the first electrode. If the surface of the first electrode is 0.06 times to 0.6 times as the area of the second electrode, the λ=1 ripple is reduced in an especially effective manner if the resistance between the first and second electrode is sufficiently low. The annular first electrode advantageously has an outer radius in the range of 1.1 to 1.7 mm, preferably 1.4 mm, and an inner radius of 0.3 to 0.9 mm, preferably 0.6 mm. The outer radius of the annular second electrode is within the range of 1.7 to 2.1 mm, in particular 1.9 mm, and the inner radius is within a range of 0.8 to 1.2 mm, preferably 1.0 mm.

In a modification of the present invention, the first and the second electrode have an elliptical form and include an elliptical recess, the ratio of main axis to auxiliary axis lying within the range of 2:1 to 1.1:1, preferably 1.5:1. In sensor elements provided with a heater, a temperature distribution develops in which elliptically shaped areas having the same temperature are formed in the large areas of the sensor element, such as on the outer surface on which the first electrode is applied. Therefore, an elliptical shaping of the electrodes achieves a reduction in the temperature differences in different regions of the electrode surface.

In an advantageous manner, the first and the second electrode include a recess in which a gas-access opening is located via which the gas gains access to the measuring-gas region. Furthermore, the sensor element has a reference-gas region, which contains a reference air having a sufficiently constant oxygen partial pressure. Located in the reference-gas region is a third electrode. The reference-gas region is advantageously provided in the plane of stratification of the measuring-gas region.

In the invention described here, the electrode is to be understood as that region of a printed circuit trace applied on a solid electrolyte member, which is in direct contact with the solid electrolyte member and is thus electrically connected to the solid electrolyte member. In contrast, the area of the printed circuit trace that is electrically insulated from the solid electrolyte member is referred to as supply line of the electrode. Consequently, the printed circuit trace is called an electrode in those regions where it is directly applied onto the solid electrolyte member and renders a contribution to the measuring signal due to its electrochemical properties. In those regions in which it is electrically insulated from the solid electrolyte member and does not contribute to the measuring signal, or only to a negligible degree, it is called a supply line to the electrode.

In a further development of the present invention, the shortest distance between the first electrode and a third electrode arranged in the reference-gas region is markedly greater than the distance between the first and the second electrode, this distance corresponding to the layer thickness of the first solid electrolyte member. An increase in the distance also causes a rise in the resistance between the first and third electrode, thereby further reducing the in-coupling of the first electrode to the third electrode and thus the λ=1 ripple. For this purpose, the supply line of the first electrode, for example, is at least regionally arranged in the section that is formed by the perpendicular projection of the second electrode onto the large surface of the first electrode. That means that the printed circuit trace of the first electrode has a partial region that is located in the area of projection of the second electrode onto the large area of the first electrode and in which an insulation electrically insulates the printed circuit trace of the first electrode from the first solid electrolyte member. In a sensor element in which the measuring-gas region and the reference-gas region are located in the same plane of stratification, the insulated partial region is advantageously provided on the side, or abutting against the side, of the first electrode facing the reference-gas region.

DETAILED DESCRIPTION

Figure 1:
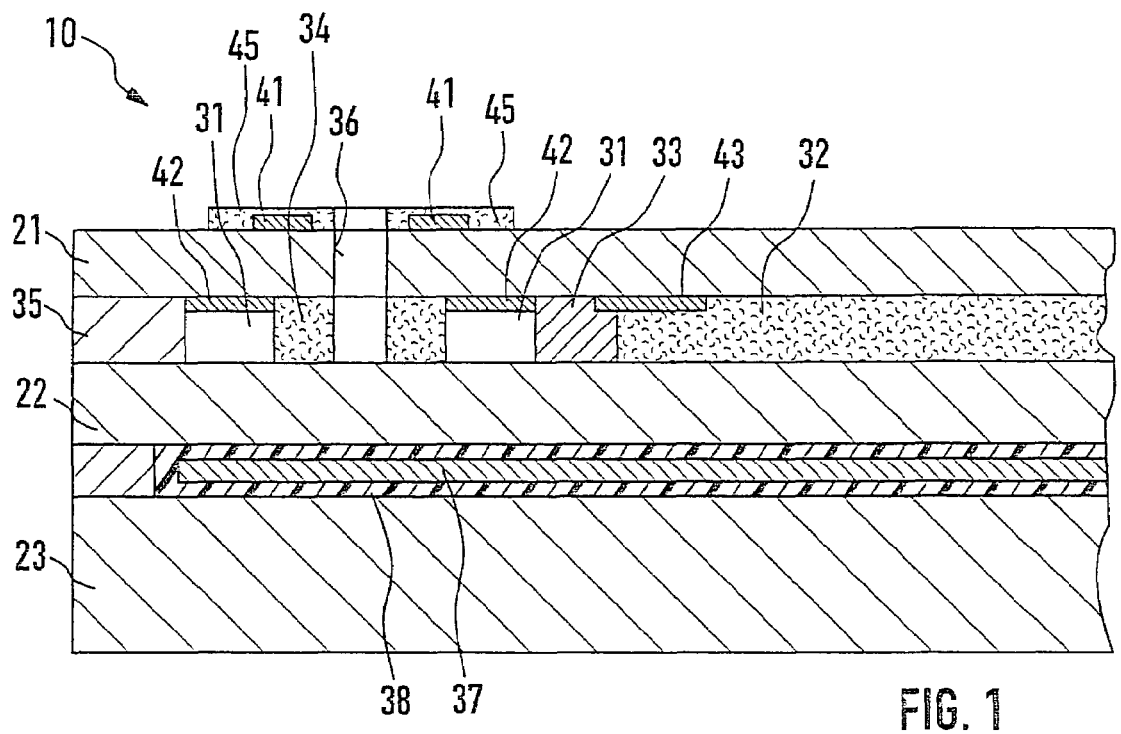
FIG. 1 shows a section along the longitudinal axis of a sensor element of a first exemplary embodiment of a gas sensor according to the present invention.

As first exemplary embodiment of the present invention, FIG. 1 shows a sensor element 10 of a gas sensor referred to as broadband lambda sensor. Sensor element 10 is configured as a layer system and includes a first, a second and a third solid electrolyte member 21, 22, 23. A gas-access opening 36 is introduced in first solid electrolyte member 21. Arranged between the first and the second solid electrolyte member is a measuring-gas region 31, a reference-gas region 32, a separation member 33, a diffusion barrier 34 and a sealing frame 35. Disposed in the center of flat, hollow-cylindrical measuring-gas region 31 is the likewise hollow-cylindrical diffusion barrier 34 in whose center gas-access opening 36 discharges. The measuring gas may reach measuring-gas region 31 through gas-access opening 36 via diffusion barrier 34. Separation member 33 forms a gas-tight barrier between measuring-gas region 31 and reference-gas region 32. Channel-shaped reference-gas region 32 contains a porous material and is in connection with a reference atmosphere on the side of sensor element 10 facing away from the measuring region. Measuring-gas region 31 and reference-gas region 32 are surrounded by a sealing frame 35 on the side.

Arranged on an outer surface of first solid electrolyte member 21 is a first electrode 41 (outer pump electrode), which is covered by a porous protective layer 45. A second electrode 42 (measuring electrode, inner pump electrode) is provided in measuring-gas region 31 on the large surface of first solid electrolyte member 21, this surface lying across from the outer surface. A third electrode 43 (reference electrode) is provided in reference-gas region 32 in the plane of stratification of second electrode 42. First electrode 41, together with second electrode 42, forms a pump cell, which pumps oxygen into or out of measuring-gas region 31 with the aid of a external circuit elements. The pump voltage present at the pump cell due to the external circuit elements is regulated such that a predefined oxygen partial pressure is present in measuring-gas region 31. An oxygen partial pressure of λ=1 is preferably adjusted, which means that the oxygen partial pressure in measuring-gas region 31 corresponds to the stoichiometric air/fuel ratio.

The oxygen partial pressure present in measuring-gas region 31 is determined by a Nernst cell, which is formed by second electrode 42 and third electrode 43. The Nernst voltage, caused by different oxygen partial pressures in measuring-gas region 31 and in reference-gas region 32, which—as described earlier—is used to regulate the pump voltage, is measured with the aid of the Nernst cell. In an alternative specific embodiment, which is not shown, the electrode associated with the Nernst cell in measuring-gas region 31 and/or the electrode associated with the Nernst cell in reference-gas region 32 may be applied on second solid electrolyte member 22. Furthermore, in addition to second and third electrodes 42, 43 arranged on first solid electrolyte member 21 in measuring-gas region 31 and/or in reference-gas region 32, at least one additional electrode associated with the Nernst cell may be arranged on second solid electrolyte member 22.

A heater 37, which is electrically insulated from surrounding solid electrolyte members 22, 23 by a heater insulation 38, is provided between second solid electrolyte member 22 and third solid electrolyte member 23.

Figure 2:
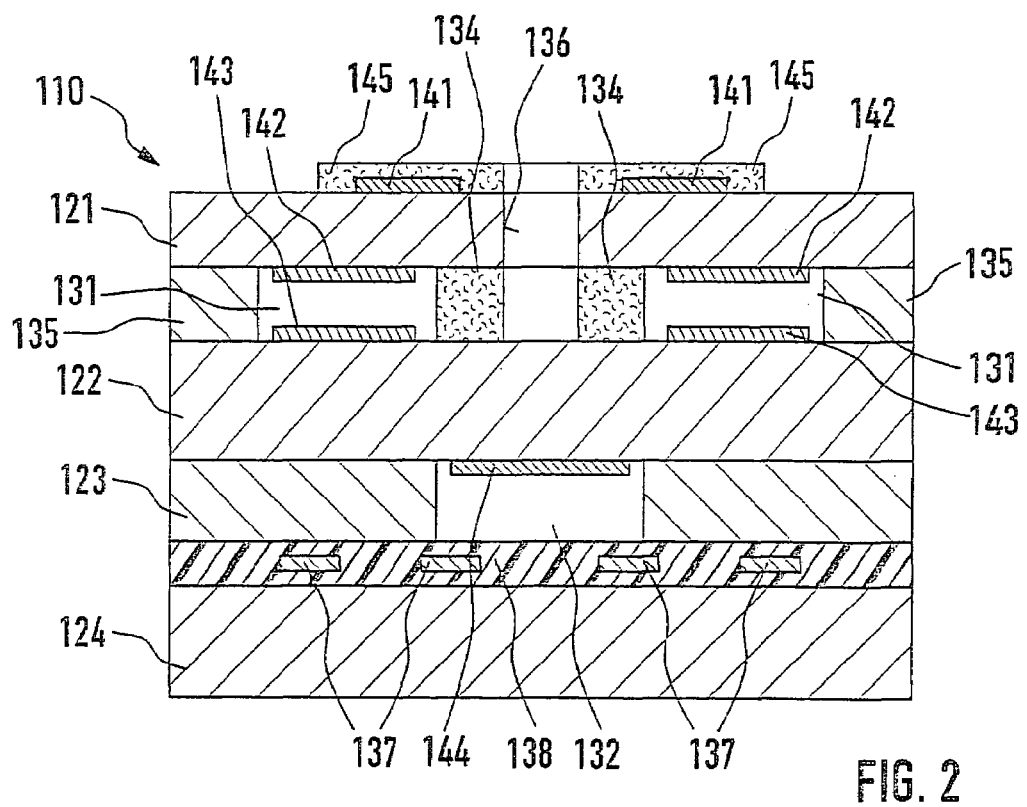
FIG. 2 shows a section perpendicular to the longitudinal axis of the sensor element of a second exemplary embodiment of the gas sensor according to the present invention.

FIG. 2 shows a second exemplary embodiment of the present invention, which differs from the first exemplary embodiment in that the measuring-gas region and the reference-gas region are not arranged in the same plane of stratification, but in different planes of stratification of sensor element 110. Sensor element 110 has a first, second, third and fourth solid electrolyte member 121, 122, 123, 124, respectively. Arranged between first and second solid electrolyte member 121, 122 are a measuring-gas region 131, a diffusion barrier 134 and a sealing frame 135. The exhaust gas reaches measuring-gas region 131 via a gas-access opening 136 introduced in first solid electrolyte member 121 and via diffusion barrier 134. A reference-gas region 132 is introduced into third solid electrolyte member 123. A heater 137, which is embedded in heater insulation 138, is arranged between third and fourth solid electrolyte member 123, 124.

Applied on the outer surface of first solid electrolyte member 121 is a first electrode 141, which is covered by a porous protective layer 145. In measuring-gas region 131, a second electrode 142 is arranged on first solid electrolyte member 121, and a third electrode 143 on the second solid electrolyte member. In reference-gas region 132, a fourth electrode 144 is provided on second solid electrolyte layer 122. First and second electrodes 141, 142 form a pump cell together with first solid electrolyte member 121; third and fourth electrodes 143, 144 form a Nernst cell together with second solid electrolyte member 122. The functioning method of these electrochemical cells corresponds to that of the first exemplary embodiment.

Figure 3:
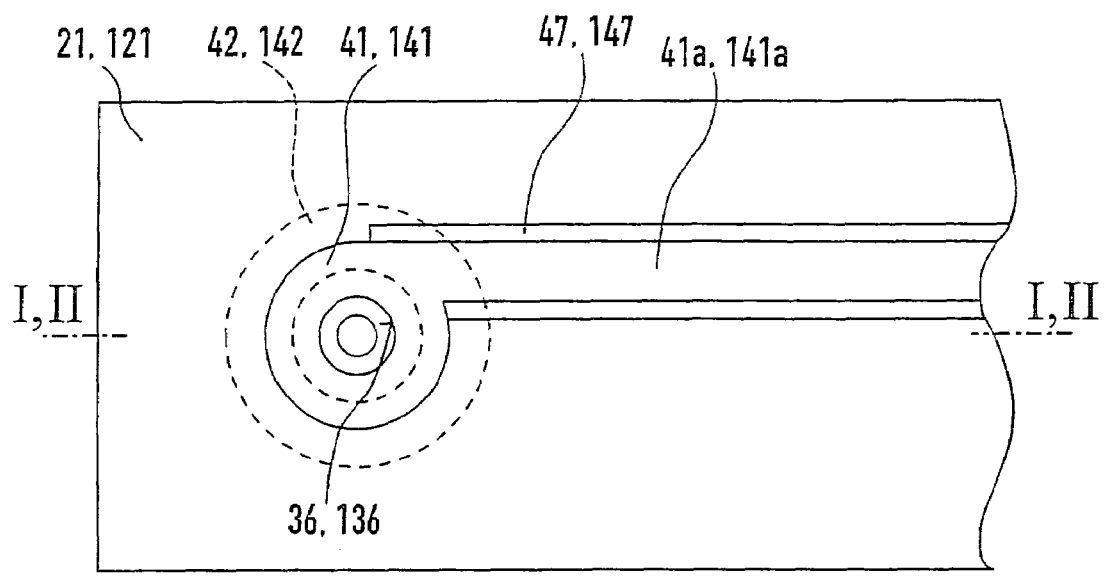
FIG. 3 shows a first plan view of the sensor element of the first and second exemplary embodiments of the present invention.

FIG. 3 shows the arrangement of first electrode 41, 141 and second electrode 42, 142 on first solid electrolyte member 21, 121 in a first embodiment of the first and second exemplary embodiments. Porous protective layer 45, 145 has been omitted to simplify the graphical representation. First electrode 41, 141 is arranged around gas-access opening 36, 136 in an annular manner. The inner radius of first electrode 41, 141 is 0.6 mm, the outer radius is 1.4 mm. Adjacent to first electrode 41, 141 is a supply line 41a, 141a, which leads to a contact surface (not shown) on the side of sensor element 10, 110 facing away from the electrodes. Via the contact surface, first electrode 41, 141 is connected to an evaluation circuit arranged outside of the gas sensor. Supply line 41a, 141a to first electrode 41, 141 is electrically insulated from first solid electrolyte member 21, 121 by an insulation layer 47, 147. Insulation layer 47, 147 follows the circular outer contour of first electrode 41, 141 in the transition area between first electrode 41, 141 and supply line 41a, 141a to first electrode 41, 141.

Second electrode 42, 142 (shown as dashed line in FIG. 3) is likewise arranged in an annular manner around gas-access opening 36, 136. Its inner diameter is 10 mm, its outer diameter 20 mm. Thus, the area of first electrode 41, 141 amounts to approximately half the area of second electrode 42, 142. Like the first electrode, second electrode 42, 142 and also the other electrodes are electrically contacted by a supply lead (not shown).

Figure 4:
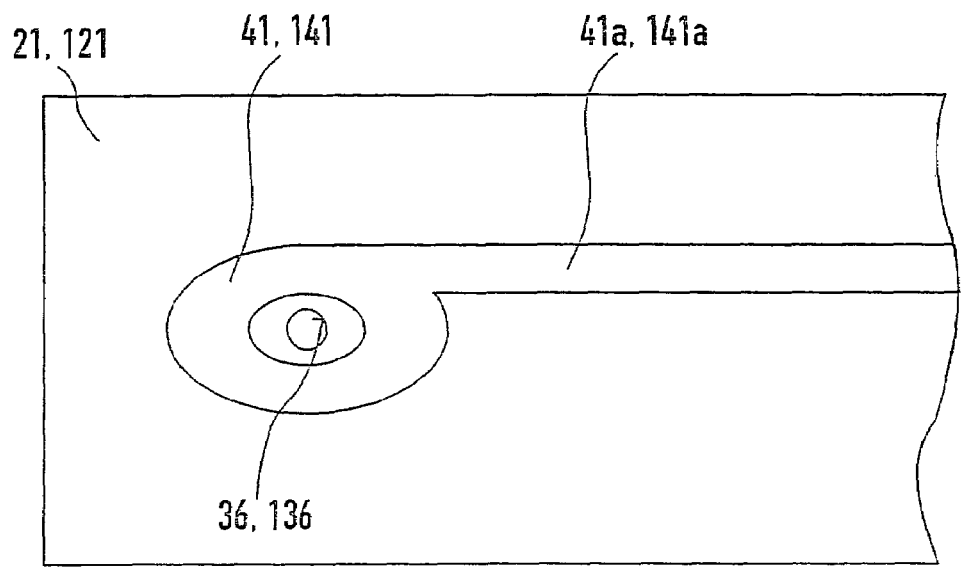
FIG. 4 shows a second plan view of the sensor element of the first and second exemplary embodiments of the present invention.

FIG. 4 shows a second specific embodiment of the first and second exemplary embodiments. To simplify the graphical representation, porous protective layer 45, 145 as well as insulation layer 47, 147 have been omitted. In the second specific embodiment, first electrode 41, 141 has an elliptical shape and includes an elliptical recess in which gas-access opening 36, 136 is arranged. The ratio of main axis to auxiliary axis both of the outer and the inner boundary of first electrode 41, 141 is 1.5:1. Like first electrode 41, 141, the second electrode (not shown) has an elliptical shape, the area of the second electrode being twice as large as the area of first electrode 41, 141. The main axes of the two ellipses of the inner and outer boundary of first electrode 41, 141 are in parallel to the longitudinal axis of sensor element 10, 110.

Figure 5:
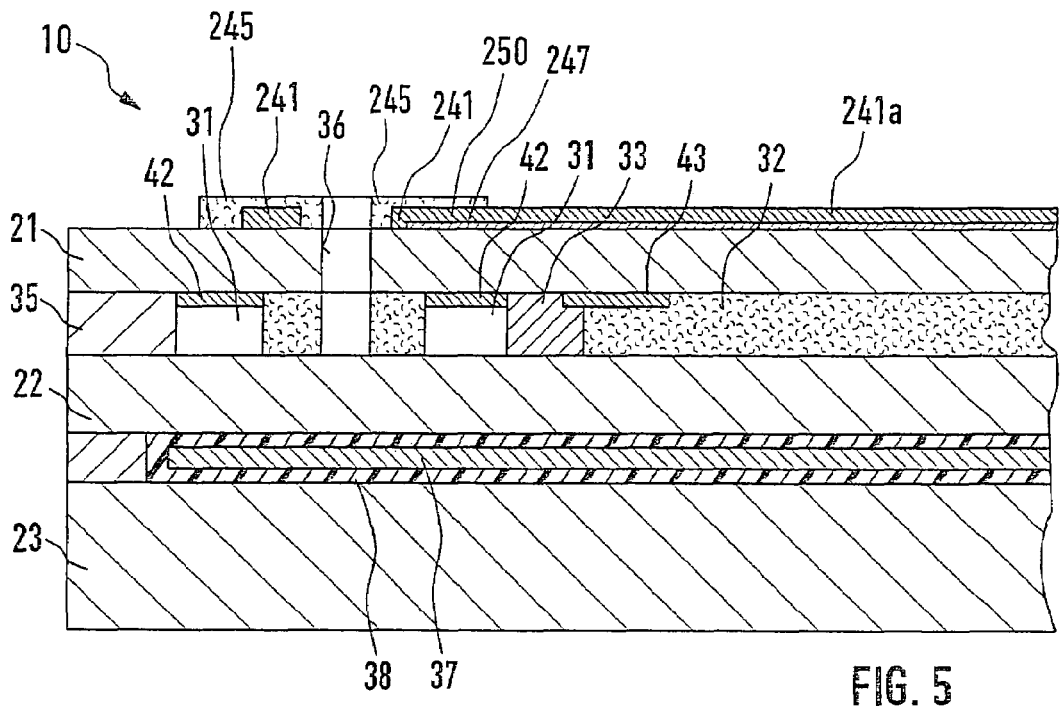
FIG. 5 shows a section along the longitudinal axis of the sensor element of a third exemplary embodiment of the gas sensor according to the present invention, along line V-V in FIG. 6.
Figure 6:
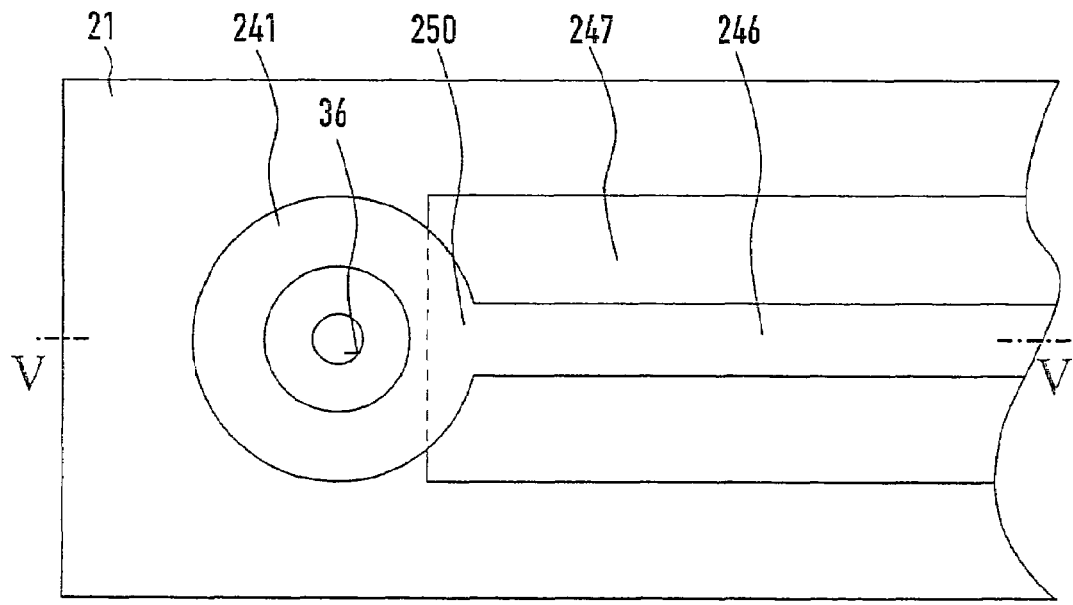
FIG. 6 shows a plan view of the sensor element of the third exemplary embodiment of the present invention.

FIG. 5 and FIG. 6 show a third exemplary embodiment of the present invention, which differ from the first exemplary embodiment in the design of first electrode 241, supply line 241a to first electrode 241, insulation layer 247 and porous protective layer 245. The other elements of the sensor element of the third exemplary embodiment have been provided with reference signs that match those of the first exemplary embodiment shown in FIG. 1.

In the third exemplary embodiment, the first printed circuit trace (that is, first electrode 241 and supply line 241a to first electrode 241) and the second printed circuit trace (that is, second electrode 42 and the supply line (not shown) to second electrode 42) have the same form, at least in the area of measuring-gas region 31 of sensor element 10. Thus, the projection of the annularly formed section of the second printed circuit trace, that is to say, essentially of electrode 42, onto the outer surface of first solid electrolyte member 21 corresponds precisely to the form of the first printed circuit trace in this region. Supply line 241a of first electrode 241 is electrically insulated from first solid electrolyte member 21 by insulation layer 247. Insulation layer 247 also extends into an insulated partial region 250 of the projection of second electrode 242 onto the outer surface of first solid electrolyte member 21. Insulated partial region 250 abuts against the side of first electrode 241 facing reference-gas region 32 and third electrode 43. Insulation layer 247 essentially consists of aluminum oxide.

Specific embodiments of the third exemplary embodiment are conceivable in which the first printed circuit trace and the second printed circuit trace do not have identical forms in the measuring region of sensor element 10 either. In particular, first electrode 241 may be smaller than second electrode 242, that is to say, it may have a smaller outer radius or a smaller inner and outer radius, or have a larger inner radius than second electrode 242.

The present invention is not restricted to the exemplary embodiments described, but may also be transferred to sensor elements having a different configuration in which malfunctions occur as a result of a high charge quantity in the region of an electrode applied in the region of an outer surface of the sensor element.

What is claimed is:

1. A gas sensor, comprising:
a first electrode;
a second electrode; and
a sensor element including a first solid electrolyte member on which the first electrode and the second electrode are arranged, the first electrode and the second electrode being electrically connected via the first solid electrolyte member, and the first electrode being in contact with a gas, wherein:
an area of the first electrode is smaller than an area of the second electrode; and
in a region of a perpendicular projection of the second electrode onto a plane of stratification of the first electrode, an insulated partial region is provided in which a printed circuit trace having the first electrode and a supply line to the first electrode is electrically insulated from the first solid electrolyte member by an insulation layer.

2. The gas sensor as recited in claim 1, wherein:
the gas includes an exhaust gas of an internal combustion engine, and
the gas sensor is for detecting at least one physical magnitude of the exhaust gas.

3. The gas sensor as recited in claim 1, wherein:
the area of the first electrode amounts to maximally 60 percent of the area of the second electrode.

4. The gas sensor as recited in claim 1, wherein:
the area of the first electrode amounts to between 5 and 30 percent of the area of the second electrode.

5. The gas sensor as recited in claim 1, wherein:
the first electrode is arranged on a surface of the sensor element facing the gas,
the second electrode is arranged in a measuring-gas region introduced in the sensor element, and
the first solid electrolyte member includes a gas-access opening via which the gas is able to enter the measuring-gas region.

6. The gas sensor as recited in claim 5, wherein:
at least one of the first electrode and the second electrode includes a recess in which the gas-access opening is arranged.

7. The gas sensor as recited in claim 5, wherein:
the first electrode extends to an edge of the gas-access opening.

8. The gas sensor as recited in claim 1, wherein:
the first electrode is at least regionally annular,
the at least regionally annular first electrode includes an outer radius in a range of 1.0 to 1.7 mm, and an inner radius in the range of 0.3 to 1.3 mm,
the second electrode is annular, and
the annular second electrode has an outer radius in the range of 1.7 to 2.1 mm, and an inner radius in the range of 0.8 to 1.2 mm.

9. The gas sensor as recited in claim 1, wherein:
the first electrode is at least regionally annular,
the at least regionally annular first electrode includes an outer radius of 1.2 mm, and an inner radius of 1.0 mm,
the second electrode is annular, and
the annular second electrode has an outer radius of 1.9 mm, and an inner radius of 1.0 mm.

10. The gas sensor as recited in claim 1, wherein:
at least one of the first electrode and the second electrode has an elliptical shape with an elliptical recess,
a ratio of a main axis to an auxiliary axis of the elliptical shape 1.5:1, and
the main axis is parallel to a longitudinal axis of the sensor element.

11. The gas sensor as recited in claim 1, wherein:
at least one of the first electrode and the second electrode has an elliptical shape with an elliptical recess, and
a ratio of a main axis to an auxiliary axis of the elliptical shape is in the range of 2:1 to 1.1:1, the main axis being parallel to a longitudinal axis of the sensor element.

12. The gas sensor as recited in claim 1, wherein:
at least one of a measuring-gas region, a reference-gas region, the second electrode arranged in the measuring-gas region, and a further electrode arranged in the reference-gas region are situated in the same plane of stratification of the sensor element.

13. The gas sensor as recited in claim 1, further comprising:
an additional electrode, wherein:
the sensor element includes an electrochemical cell corresponding to a Nernst cell,
the Nernst cell includes in a measuring gas region the second electrode, and
the second electrode and the additional electrode are electrically connected by the first solid electrolyte member.

14. The gas sensor as recited in claim 1, wherein:
the second electrode is arranged in a measuring-gas region introduced in the sensor element,
a reference-gas region is provided in a plane of stratification of the measuring-gas region, and
the insulated partial region is provided so as to abut a side of the first electrode facing the reference-gas region.

15. The gas sensor as recited in claim 1, further comprising:
a third electrode arranged in a reference-gas region, wherein:
a shortest distance between the first electrode and the third electrode is larger by at least 50% than a layer thickness of the first solid electrolyte member.

* * * * *